United States Patent
Baillie et al.

(10) Patent No.: US 7,060,354 B2
(45) Date of Patent: *Jun. 13, 2006

(54) DENTAL FLOSS HAVING LOW DENSITY AND METHOD OF MAKING SAME

(75) Inventors: Richard L. Baillie, Newark, DE (US); James H. Chastain, Cottonwood, AZ (US); John W. Dolan, Wilmington, DE (US); William Hammond Wiley, Flagstaff, AZ (US)

(73) Assignee: Gore Enterprise Holdings, Inc., Newark, DE (US)

(*) Notice: Subject to any disclaimer, the term of this patent is extended or adjusted under 35 U.S.C. 154(b) by 186 days.

This patent is subject to a terminal disclaimer.

(21) Appl. No.: 10/339,787

(22) Filed: Jan. 9, 2003

(65) Prior Publication Data

US 2003/0172951 A1 Sep. 18, 2003

Related U.S. Application Data

(63) Continuation of application No. 09/449,078, filed on Nov. 24, 1999, now Pat. No. 6,539,951, which is a continuation-in-part of application No. 09/387,691, filed on Aug. 31, 1999, now abandoned.

(51) Int. Cl.
*D01F 6/00* (2006.01)

(52) U.S. Cl. .................. 428/364; 428/421; 428/394; 132/321

(58) Field of Classification Search .................. 428/364, 428/421, 394; 132/321
See application file for complete search history.

(56) References Cited

U.S. PATENT DOCUMENTS

| | | | |
|---|---|---|---|
| 3,953,566 A | 4/1976 | Gore | 264/288 |
| 3,962,153 A | 6/1976 | Gore | 260/2.5 R |
| 4,187,390 A * | 2/1980 | Gore | 174/102 R |
| 4,598,011 A | 7/1986 | Bowman | 428/221 |
| 4,996,056 A | 2/1991 | Blass | 424/443 |
| 5,296,292 A | 3/1994 | Butters | 428/375 |
| 5,518,012 A | 5/1996 | Dolan et al. | 132/321 |
| 5,657,779 A | 8/1997 | Blass et al. | 132/321 |
| 5,718,251 A | 2/1998 | Gray et al. | 132/321 |
| 5,765,576 A | 6/1998 | Dolan et al. | 132/321 |
| 5,800,823 A | 9/1998 | Blass | 424/400 |
| 5,806,539 A | 9/1998 | Blass et al. | 132/321 |
| 5,819,768 A | 10/1998 | Bible et al. | 132/321 |
| 5,851,454 A | 12/1998 | Rutkowski et al. | 264/8 |
| 5,878,758 A | 3/1999 | Bacino et al. | 132/321 |
| 5,908,039 A | 6/1999 | Ochs et al. | 132/321 |
| 5,911,228 A | 6/1999 | Curtis et al. | 132/321 |
| 6,220,256 B1 | 4/2001 | Dolan et al. | 132/323 |
| 6,539,951 B1 * | 4/2003 | Baillie et al. | 132/321 |

FOREIGN PATENT DOCUMENTS

| | | |
|---|---|---|
| EP | 922440 A2 | 6/1999 |
| GB | 2320449 | 6/1998 |
| WO | WO 00/48528 | 8/2000 |

* cited by examiner

*Primary Examiner*—N. Edwards
(74) *Attorney, Agent, or Firm*—Dianne Burkhard (57) ABSTRACT

A dental floss comprising a porous PTFE fiber having a density of less than about 0.7 g/cc. The inventive floss is abrasion resistant, grippable and has a soft feel to the hands and a rough feel in the mouth. The floss is made by an extrusion process with non-contact heating during subsequent expansion with amorphous locking.

49 Claims, 8 Drawing Sheets

VHF 100 x

VHF 500x

DENTAL FLOSS HAVING LOW DENSITY AND METHOD OF MAKING SAME

RELATED APPLICATIONS

This application is a continuation of application Ser. No. 09/449,078, filed Nov. 24, 1999, now U.S. Pat. No. 6,539,951, which is a continuation-in-part of application Ser. No. 09/387,691, filed Aug. 31, 1999 now abandoned.

FIELD OF THE INVENTION

The present invention relates to dental floss and, more particularly, to a dental floss having a low density.

BACKGROUND OF THE INVENTION

Use of dental floss remains one of the most recommended ways of preventing and controlling gum disease. Several types of floss are currently known and used. These flosses are made of materials such as nylon, polyethylene, ultra-high molecular weight polyethylene, polytetrafluoroethylene (PTFE), and expanded PTFE (ePTFE). Of these, ePTFE floss, and particularly monofilament ePTFE floss, is particularly preferred, in part because of its inherently low friction properties which allow it to slide between teeth more easily.

Certain characteristics are typically considered desirable for dental floss. First, the floss should be abrasion resistant such that it does not shred, fray, or otherwise break during use when passed between a user's teeth. In order to be used effectively, the dental floss should also be grippable; that is, able to be grasped by a user's hands or other device for manipulation between the teeth without slipping in the hands or other device. Several attempts have been made at making PTFE flosses more easily grippable. As discussed in U.S. Pat. No. 5,518,012 to Dolan, et al., for example, a waxed coating may be placed over the PTFE fiber in order to make the floss more grippable. In U.S. Pat. No. 5,911,228 to Curtis, et al, a solid additive is incorporated within the PTFE fiber structure in order to make the fiber grippable without the need for any coating. A grippable PTFE floss that did not require the use of either a coating on the fiber or additives within the fiber in order to make it grippable, would be desirable.

A dental floss should also have the subjective advantage of having a good "feel" for the user. The feel includes the overall handling characteristics of the fiber as well as the perceived effect of the fiber in a user's mouth as it cleans the teeth. Desirably, a PTFE dental floss should be soft and conformable to slide comfortably between a user's teeth, while at the same time providing a scrubbing or cleaning sensation for the user when manipulated under the gums. The floss should have a soft feel to the hands and a rough feel in the mouth.

A PTFE floss having all of these advantages and characteristics would be desirable.

SUMMARY OF THE INVENTION

The present invention provides a dental floss comprising a fiber having a denier between 100 and 3,500 and having a density of less than about 0.8 g/cc, with additional ranges for alternative embodiments of less than about 0.7 g/cc, less than about 0.6 g/cc, less than about 0.5 g/cc, less than about 0.4 g/cc, less than about 0.3 g/cc, and less than about 0.2 g/cc. The floss has a strength suitable for use as a dental floss, typically greater than about 1.5 lbs, with additional ranges for alternative embodiments of greater than about 2 lbs, greater than about 2.5 lbs, greater than about 3 lbs, greater than about 5 lbs, greater than about 7.5 lbs, and greater than about 10 lbs. The floss may be a hollow fiber with any desired cross-section, such as substantially elliptical or rectangular. The floss is also abrasion resistant, having an average abrasion break strength in various embodiments of greater than $2.8 \times 10^{-3}$ lbs. per denier, greater than $3.0 \times 10^{-3}$ lbs. per denier, greater than $4.0 \times 10^{-3}$ lbs. per denier, greater than $5.0 \times 10^{-3}$ lbs. per denier, or greater than $6.0 \times 10^{-3}$ lbs. per denier. The inventive floss has increased surface roughness with an average roughness greater than about 0.3 microns (preferably about 1.3 microns), a root mean square roughness of greater than about 0.35 microns (preferably about 1.6 microns), and a peak to valley distance of greater than about 1.7 microns (preferably about 6.3 microns). The dental floss may be any material suitable for a floss, and porous PTFE is preferred, particularly expanded PTFE. There may be a plurality of fibers in the floss, each with the same or different composition. The floss may include a filler.

In another aspect, the present invention provides a method of making a dental floss including the steps of providing a PTFE resin, extruding said resin to form an extrudate, and expanding the extrudate into a fiber having the properties presented above. The extrusion is performed in the preferred embodiment with a mandrel in the extruder. Reduction ratios in the extruder in various embodiments may be greater than 150 to 1, greater than 200 to 1, greater than 250 to 1, greater than 300 to 1, or greater than 500 to 1. The extrudate is heated during expansion by non-contact heating such that the extrudate does not touch the heat source during the process.

In still another aspect, the present invention provides a filament having the properties and composition presented above.

In still further aspects, the present invention provides an improved sewing thread, a fiber for weaving, and a filament for structures in bearing and bushing applications.

DETAILED DESCRIPTION OF THE INVENTION

The present invention provides an ePTFE dental floss having a density less than 0.8 g/cc. The inventive floss is abrasion resistant, grippable, and has a good feel for the user.

PTFE dental floss is typically made by extruding and expanding a relatively large tape of PTFE, and then slitting the tape into fibers of the desired size for the dental floss. Such a production method is described, for example, in U.S. Pat. No. 5,518,012 to Dolan et al. According to the present invention, the inventive dental floss is produced by a novel method.

Specifically, according to the present invention, PTFE dental floss is produced by extruding a PTFE fiber (as opposed to a tape) of desired dimensions and then expanding the fiber to produce a node and fibril structure within the fiber that is characteristic of expanded PTFE. The expanded fiber has the desired final dimensions of the floss. In that manner, the floss fiber itself is produced from the extruder without the necessity of an intervening slitting step.

Figure 3:
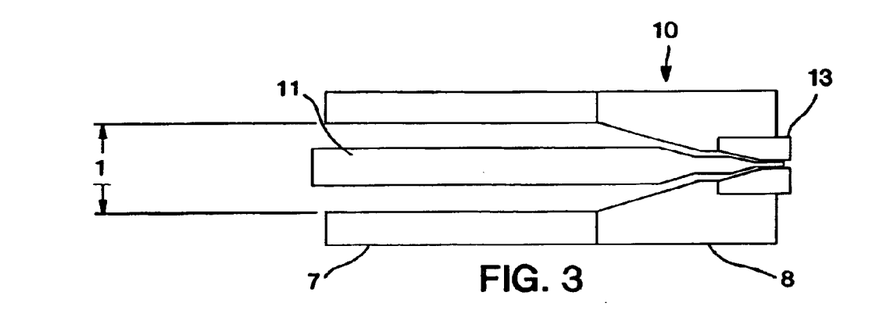
FIG. 3 is a side cross-sectional view of an extruder used to produce the fiber according to this invention.
Figure 3A:
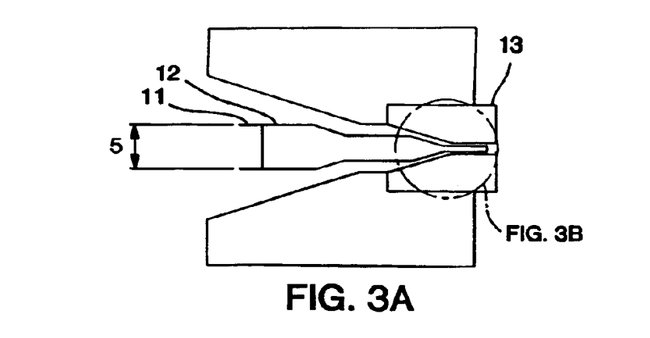
FIG. 3A is a side cross-sectional view of a portion of the extruder illustrated in FIG. 3.
Figure 3B:
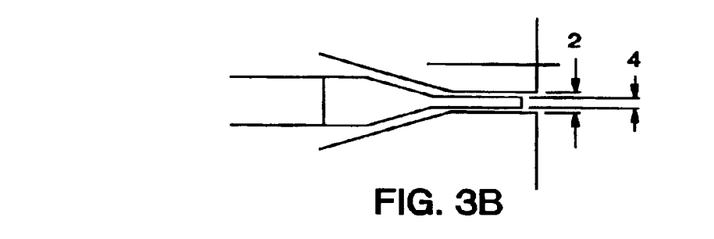
FIG. 3B is a detail of a portion of FIG. 3A.
Figure 3C:
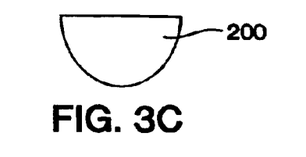
FIG. 3C is a detail of the tip extension used in Example 2.

A PTFE fiber dental floss according to the present invention is produced as follows. A PTFE resin is prepared for extrusion according to methods known in the art, such as those described in U.S. Pat. No. 3,953,566 to Gore, the disclosure of which is incorporated herein by reference. The extruder may be a conventional paste tubing extruder such as that shown at 10 in FIG. 3. Extruder 10 includes a mandrel 11 in the center portion thereof. Mandrel 11 has a tip 12 (FIG. 3A) that extends into a die 13 at the opening of extruder 10. Extruder 10 has barrel 7 and transition 8. The barrel has an inner diameter 1 as shown. FIG. 3A illustrates the mandrel diameter 5. FIG. 3B illustrates the included die land diameter dimension 2, and the tip land diameter dimension 4. FIG. 3C illustrates the flattened tip land.

Mandrel 11 (and hence tip 12) may extend completely into die 13 such that the extrudate from extruder 10 is hollow. Alternatively, mandrel 11 (and hence tip 12) may be withdrawn from die 13 back into extruder 10 itself to reduce the relative size of the center hole or bore within the extrudate or to provide a non-hollow cross-section. An important aspect of the present invention is that the PTFE is exposed to significant working during extrusion. The amount of work imparted to the polymer is affected by the reduction ratio of the extruder. The reduction ratio is represented by the working area of the extruder divided by the area of the die. To achieve the desired properties of the present invention, it is desirable that the reduction ratio be greater than 150:1, preferably greater than 200:1, more preferably greater than 250:1, still more preferably greater than 300:1, and most preferably greater than 500:1.

Whether a hollow fiber is produced or not according to this invention, and without being limited by theory, it is believed that use of mandrel 11 with tip 12 in the extrusion of a PTFE fiber provides additional work to the PTFE that contributes to the beneficial properties of the extrudate described herein.

Any desired operating conditions of extruder 10 may be used to produce a suitable extrudate. Preferred conditions are set forth in the examples herein.

Figure 4:
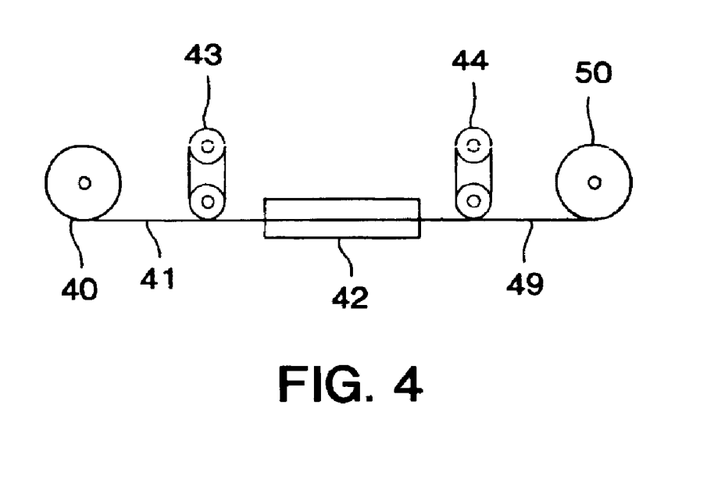
FIG. 4 is a side view of equipment used in an exemplary embodiment of the process according to the present invention.
Figure 5:
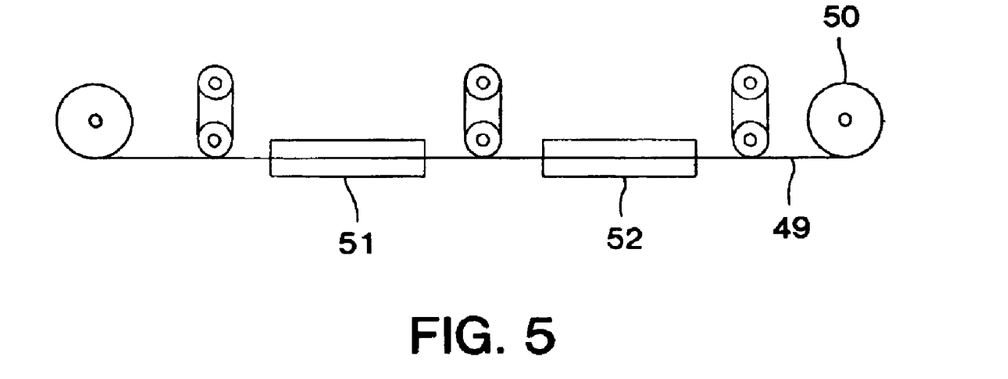
FIG. 5 is a side view of equipment used in another exemplary embodiment of the process according to the present invention.

After exiting extruder 10, the extrudate is spooled up on a take-up spool 40 (FIG. 4). The extrudate (shown at 41 in FIG. 4) is then paid off spool 40 and passed through an oven 42, preferably a forced convection oven. Capstans 43 and 44 are preferably used to control the rate of extrudate 41 through oven 42. The extrudate is expanded as it passes through oven 42. Any desired expansion (or stretch) ratio (determined by the capstan speed ratio) may be used; for example, from 2 to 1 to 120 to 1 or greater. In an alternative embodiment, two separate ovens 51 and 52 as shown in FIG. 5, and two separate corresponding expansions, may be used. In either event, the process produces the inventive fiber 49, which may then be taken up on final take-up spool 50.

An important feature of the invention is that all of the heating of extrudate 41 (or fiber 49) occurs without contacting extrudate 41. Specifically, the present invention uses forced convection oven 42 (or 51 and 52) through which extrudate 41 passes without contacting the walls of the oven. This is in contrast to the currently accepted method of producing PTFE dental floss that involves dragging a fiber over a heated plate in order to effect the heat transfer. Without being limited by theory, it is believed that such contact with a heated plate smears or otherwise smoothes the surface of the PTFE fiber, thereby contributing to the low surface friction and difficult grippability of conventional PTFE flosses. As discussed in greater detail below, the non-contact heating of the fiber of the present invention is believed to help produce a rougher surface on the fiber than is achieved with plate contact heating. This rougher surface in turn contributes to higher surface friction and better grippability for the inventive floss.

After expansion, the fiber has the desired final characteristics of a dental floss. These final characteristics are, for example, a thickness (designated "B" in FIG. 1) of 0.0015" to 0.04", a width (designated "A" in FIG. 1) of 0.3 to 4 mm (0.01" to 0.16"), and a denier of 100 to 3,500. Most importantly, the fiber should have a density of less than 0.8 g/cc, and in alternative embodiments less than about 0.7 g/cc, less than about 0.6 g/cc, less than about 0.5 g/cc, less than about 0.4 g/cc, less than about 0.3 g/cc, and less than about 0.2 g/cc. Each of these properties is measured in a conventional manner. Thickness may be determined through any conventional means, such as through the use of calipers, a snap gage, optical comparitors, or even a scanning electron microscope. Density may be determined by dividing the measured mass of a sample of fiber (without any coating or additive) by the computed volume of the sample. Volume may be computed by multiplying the measured length, width, and thickness of the sample for substantially rectangular cross-sections, or by other known calculations for other cross-sectional shapes to obtain the most accurate approximation of the volume. Denier is the measured mass of the sample (without any coating or additive) in grams per 9000 meters of length.

Figure 6:
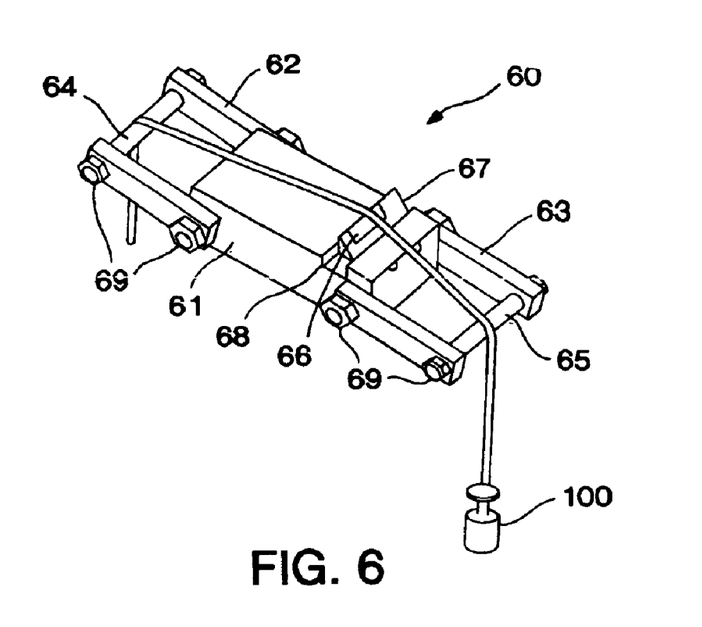
FIG. 6 is a perspective view of test apparatus used to measure the abrasion resistance of dental floss.

The floss produced according to this method also has improved abrasion resistance. Abrasion resistance is measured using the device 60 illustrated in FIGS. 6 and 7. Device 60 has a base 61 made of stainless steel. Extension assemblies 62 and 63 project from base 61 and are adjustably attached thereto by bolts 69. Each extension assembly 62 and 63 has a roller 64, 65 attached thereto by bolts 69. A micro grain carbide blade 66, part number AL-8 available from Micro-100, Inc. Los Angles, Calif., is supported on support 67 mounted in a groove 68 formed in base 61.

Figure 7:
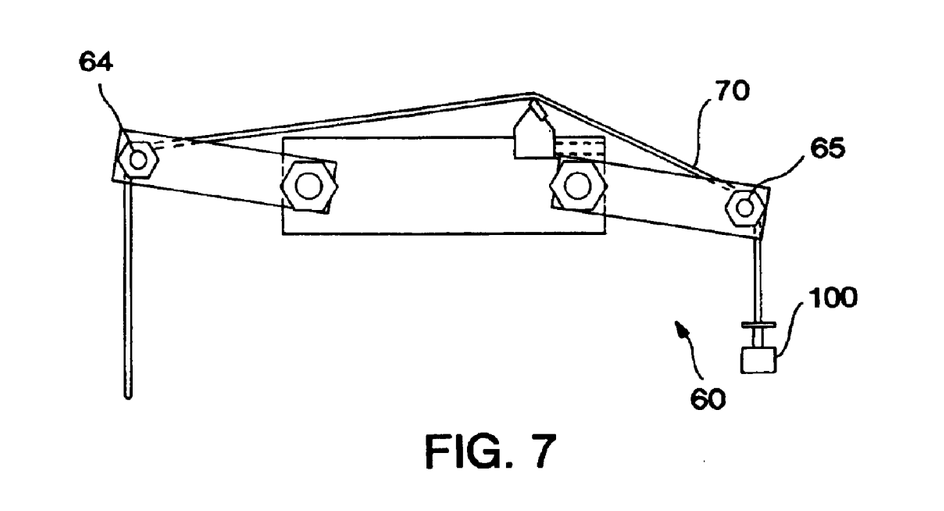
FIG. 7 is a side view of the test apparatus of FIG. 6.

As shown in FIG. 7, a sample of floss 70 is laid over device 60 such that floss 70 contacts device 60 at three points: at roller 64, blade 66, and roller 65. The angle of extension assemblies 62 and 63 is set so that floss 70 is as close as possible to base 61 without actually touching base 61. One end of floss 70 is attached to a 429 gram mass 100 and the other end of floss 70 is attached to a reciprocating linear actuator (not shown) that repeatedly pulls floss 70 over device 60. The reciprocating linear actuator has a stroke length of ¹³⁄₁₆″ and a rate of 1.5 strokes per second (each stroke is one back-and-forth cycle). Ten strokes are made. The reciprocating linear actuator is then stopped, and floss 70 is removed from blade 66, which is wiped with a clean cotton towel. Floss 70 is then remounted and ten more strokes are run. The reciprocating linear actuator is then stopped, and floss 70 is again removed, blade 66 is again wiped with a clean cotton towel, and floss 70 is then remounted and ten final strokes are run. Thus, a total of 30 strokes are made with 2 intermittent cleaning wipes.

Floss 70 is removed from device 60 and extended between fiber jaws (horn type) of an Instron Model 1130, available from Instron Co., Canton, Mass. Floss 70 is mounted with its abraded portion centered between the jaws. The gauge length of the Instron is 10″ and the cross-head speed is 10″ per minute. The load at break (in pounds-force) is measured and recorded for each sample tested as "abrasion break strength." Five such tests (abrading and breaking) are run on lengths of each fiber sample, and the average of the five is reported. The abrasion break strength may be divided by the denier of the tested sample to produce a denier-normalized break strength. The term "abrasion resistant" as used herein means having a denier-normalized break strength according to the above test of greater than about $2.8 \times 10^{-3}$ lbs./denier. Data for the tested samples is reported in Table 7.

The inventive floss is considerably more grippable than conventional PTFE fibers. Accordingly, the floss of the present invention may serve some flossing functions, such as use in a floss pick, without the need for any grip-enhancing coating or additive. It may be desirable, however, to include a light wax coating (such as 2–3% by weight of beeswax or any other known grip-enhancing coating or additive) on the floss of the current invention to further enhance grippability. Because of the increased grippability of the fiber itself, however, considerably less wax or other additive or coating need be applied to the floss of the current invention compared to the amount necessary with conventional PTFE flosses.

Without being limited by theory, it is believed that the improved grippability of the inventive floss is a result of its increased surface roughness and lower density over conventional PTFE flosses. This increased surface roughness of the present fiber, which is at least partially a result of the non-contact heating of the fiber according to the inventive method, is illustrated in the scanning electron micrographs discussed below.

The surface roughness of the fibers is measured by profilometry. Measurements are taken from 500 micron by 500 micron square representative areas on the width side (designated "A" in FIGS. 1 and 2) of the sample.

Profilometery measurements were made with a Tencor Profiler Model P_10, which provides samples over a 500× 500 micron area. The Tencor Profiler was equipped with a MicroHead sr Exchangeable Measurement Head (stylus tip radius of 20 microns with an angle of 60 degrees). Menu recipe settings for the prolfilometer were as follows:

| | |
|---|---|
| Scan length: | 500 microns |
| Data spacing in x: | 0.40 microns |
| Data spacing in y: | 0.20 microns |
| Noise filter cutoff: | .250 microns |
| Waviness cutoff filter | 250 microns |

Surface roughness measurements are reported below.

The tensile strength (also referred to herein as "break strength" or simply as "strength") of the inventive floss should be suitable for use as a floss. Desirable strength is greater than 1.5 lbs. Preferably, the strength is greater than 2.0 lbs, greater than 2.5 lbs, greater than 3.0 lbs, greater than 5.0 lbs, greater than 7.5 lbs, or greater than 10 lbs. The strength of the floss is measured by a tensile tester, such as the INSTRON machine mentioned above. The cross-head speed of the tensile tester is 10″ per minute. The gauge length was 10″ measured from tangent point to tangent point on horn-type jaws. The strength is considered to be maximum load on the fiber during the test.

Matrix tensile strength of porous PTFE samples is determined by the formula:

(2.2 g/cc×tensile strength)/density, where 2.2 g/cc is taken to be the density of non-porous PTFE.

Tenacity is computed by converting the break strength from lb-force to gram-force and dividing the filament's break strength in gram-force by the filament's denier.

The elongation of the fibers is calculated by the Instron machine. Strain is calculated by dividing the length of the sample in the Instron machine at failure by the original length of the sample.

Figure 1:
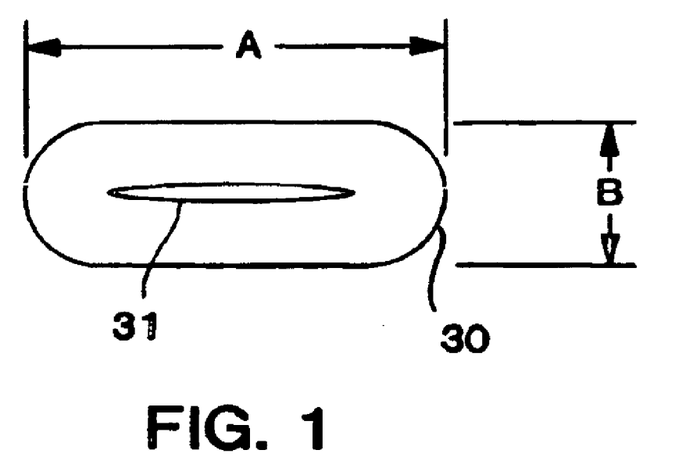
FIG. 1 is a cross-section of a dental floss according to an exemplary embodiment of the present invention.

A cross-section of an exemplary fiber made according to this invention is shown in FIG. 1. Fiber 20 has a substantially rectangular cross-section in FIG. 1. Upon extrusion from the extruder 10, the extrudate may have a round cross-section, but after the extrudate is stretched into a fiber and wound onto a spool, it is compressed somewhat to the substantially rectangular shape shown in FIG. 1. It will be appreciated by those skilled in the extrusion art that extrudate and fiber of any cross-sectional shape may be produced.

Figure 2:
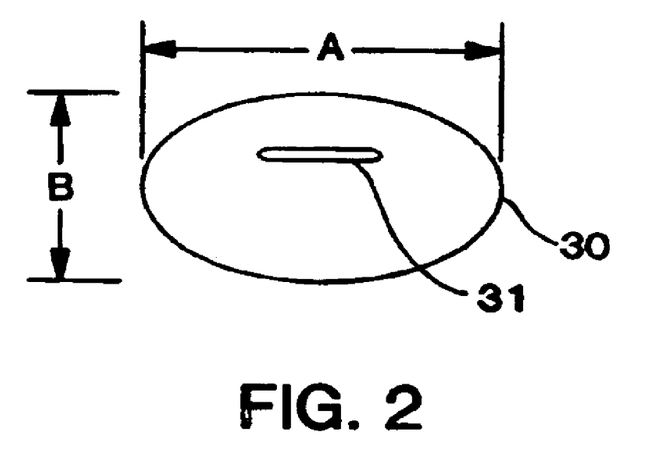
FIG. 2 is a cross-section of a dental floss according to another exemplary embodiment of the present invention.

FIG. 2 shows another exemplary fiber 30 formed according to the process described above wherein the mandrel is inserted into the die far enough to produce a hollow cross-section. Although the hollow core of the fiber may ultimately be compressed after the fiber is expanded and wound onto the spool, the fiber initially has an opening 31 in the center of fiber 30 upon exiting extruder 10. In FIGS. 1 and 2, the width dimension is generally designated as A and the thickness dimension is generally designated as B. The cross-sectional area is calculated as A×B for such substantially rectangular cross-sections. These dimensions are used in calculating the density as described above.

Although PTFE, and in particular expanded PTFE, is the preferred material for use as the floss according to this invention, other materials including polymers such as polyethylene, ultra-high molecular weight polyethylene, polypropylene, and nylon may be used to produce floss having the inventive properties defined herein.

Any inventive fiber produced according to this invention may optionally include one or more fillers, also referred to as additives. The fiber has a structure of nodes interconnected by fibrils defining interconnected passages and pathways. A filler may be included in the matrix of the ePTFE itself, or contained within the passages and pathways defined by the structure, or both. In the case of the inventive fiber with a hollow core (also referred to herein as a center bore or hole), a filler may also or alternatively be contained within the center bore.

Desirable fillers or additives may include colorants, flavorants, medicants, anti-microbials, antibiotics, antibacterial agents, antifungals, dentifrice, remineralizing agents, whitening agents, immunological agents, anti-tartar or anti-caries agents, anti-plaque agents, lysozmes, anti-inflammatory agents, hemostatic agents, analgesics, sodium fluoride, zinc chloride, tetrasodium pyrophosphate, sodium acid pyrophosphate, tetrapotassium pyrophosphate, vitamin K, water soluble calcium salts, blood factors that initiate the coagulation cascade, aminocaproic acid, tranexamic acid, adrenaline, alum, noradrenaline, iron salts and calcium alginate, sodium monofluorophosphate, stannous fluoride, chlorhexidine, hexachlorophene, cetyl pyridinium chloride, benzethonium chloride, ureases, calcium carbonate, magnesium carbonate, orthophosphoric acid, monosodium phosphate, monopotassium phosphate, disodium phosphate, dipotassium phosphate, hemisodium phosphate, benzothonium, chloride, acetyl trimethyl ammonium bromide, sanguinaria, triclosan, tetracycline, cetyl pyridinium chloride, benzothonium chloride, melt emulsion of dimethicone, and mixtures thereof. Any suitable gripping agent, such as silica, fumed silica, or sodium fluoride, or coating, such as wax, may also be used in order to make the inventive floss easier to grip, although as discussed herein, the inventive floss is more grippable than conventional flosses without such agent or coating.

The following examples are presented by way of further explanation and they are not intended, nor should they been interpreted, to limit the invention in any way.

EXAMPLE 1 (HOLLOW FLOSS EXAMPLE)

Five pounds of CD123 PTFE resin available from ICI, Wilmington, Del., was sifted through a 10-mesh screen into a 2-gallon carboy and blended with 675 ml of Isopar K. (22.6% by weight of lube over dry weight of PTFE resin). The carboy was placed on an inclined plane tumble blender and tumbled for 30 minutes. The carboy was then removed from the blender and allowed to sit overnight before pelletizing. The pre-form was compressed to a pressure of 300 psi, removed from the pelletizer and placed in a sealed tube to allow preheating. The pre-form was heated to 40 degrees C. for a period of 16 hours before extrusion. The extruder used was a conventional paste tubing extruder using a 2-inch barrel. The barrel and die temperature were set to 40 degrees C. The die used for the experiment had a land diameter of 0.153 inches. The tip used had a land diameter of 0.142 inches and was held in place by a 0.750 inch mandrel. The calculated reduction ratio for the set up was 1095 to 1. A wet extrudate was produced. The wet extrudate was taken up on a spool with a 4-inch core diameter using only enough tension to prevent slack from forming between the extruder and the spool. The extrusion rate was about 40 feet per minute. The wall thickness of the extrudate was about 0.013 inch including die swell. The spool of wet extrudate was placed on a tension payoff and fed around a set of capstan wheels 5 inches in diameter. From the capstan, the extrudate was then passed through a forced convection oven 4 feet long with an inner diameter of 1 inch without contacting the walls of the oven. After leaving the oven, the extrudate was wrapped around a set of capstan wheels 7 inches in diameter. From the capstan wheels the extrudate was then passed through a second forced convection oven 4 feet long with an inner diameter of 1 inch without contacting the walls of the oven. After leaving the oven, the extrudate was then wrapped around a set of capstan wheels 7 inches in diameter and to a tension take-up using a 7.5-inch core diameter spool. The ovens were countercurrent flow ovens set to an airflow of 9 cubic feet per minute. The temperature at the fiber exit of the ovens was set at 380 degrees C. and the temperature at the fiber inlet of the ovens was set at 220 degrees C. An initial speed ratio of 5 to 1 was set between the capstan 1 and capstan 2 with the first capstan rate set to 2 feet per minute. The first capstan rate was maintained at 2 feet per minute for the entire test. The speed ratio between capstan 2 and capstan 3 was set to 1.2 to 1 for this example. The ratio between the capstan 1 and capstan 2 was then raised in steps of 5 until a speed ratio of 15 to 1 was established. A length of material was run at this setting before raising the speed ratio to 20 to 1. This process was repeated for speed ratios of 25 to 1 and 30 to 1. The oven temperatures were raised along with the speed ratio, starting at the speed ratio of 15 to 1, in 5-degree increments to maintain amorphous locking of the material. At the speed ratio between capstan 1 and capstan 3 of 36 to 1, the rate at the third capstans was 72 ft/min and the temperature of the fiber exit of the ovens was 400 degrees C. Markers were placed on the extrudate as it was taken up to identify where changes were made. As it was taken up on a spool, the fiber tended to flatten out to substantially the shape shown in FIG. 1. The fiber obtained by this process was tested for width, thickness, denier, and strength. The results are reported in Table 1 (Before the strength was measured, the samples were coated with 2% natural beeswax. The beeswax was applied to the samples using a winding and waxing machine model CE-1487 available from Cezoma International, Inc., Spring City, Pa. The beeswax was heated to 97 degrees Celcius before it was applied to the samples.)

EXAMPLE 2 (HOLLOW, SUBSTANTIALLY ELLIPTICAL CROSS-SECTION EXAMPLE)

Using the same blended resin as in Example 1, an extrusion was done with the same die as in Example 1 and used a flattened tip having a profile as shown at 200 in FIG. 3C. The reduction ratio for this setup was about 265:1. The extrudate had a 'D' shaped hole through its length to form the hollow fiber. The spool of wet extrudate was placed on a tension payoff and processed in manner similar to Example 1. The speed ratio between capstan 1 and capstan 2 was fixed at 4 to 1 and the speed ratio between capstan 2 and capstan 3 varied as listed in Table 2. As it was taken up on a spool, the fiber tended to flatten out to substantially the shape shown in FIG. 2. The spool of fiber produced according to this Example 2 were tested for width, thickness, denier, and strength, and the results are reported in Table 2. (Before the strength was measured, the samples were coated with 2% natural beeswax as described in connection with Example 1.)

EXAMPLE 3 (NON-HOLLOW, SUBSTANTIALLY RECTANGULAR CROSS-SECTION EXAMPLE)

Using the same blended resin as in Example 1, an extrusion was done using a 0.075" by 0.037" rectangular die land cross section. The tip tapered to a point and was withdrawn from contact approximately 0.5 inches to allow a rectangular bead (non-hollow) to be extruded. The barrel size was 0.850 inches and the mandrel was 0.315 inch, giving a calculated reduction ratio of 176 to 1. The barrel and die temperature was set to 45 degrees C. for this example. The wet extrudate was taken up using the method of Example 1. The spool of wet extrudate was placed on a tension payoff and processed in manner similar to example 1. The speed ratios used for this Example 3 are noted in Table 3. The fiber obtained using this process was tested for width, thickness, denier, and strength. The results are reported in Table 3. (Before the strength was measured, the samples were coated with 2% natural beeswax as described in connection with Example 1.)

EXAMPLE 4 (NON-HOLLOW, SUBSTANTIALLY ROUND CROSS-SECTION EXAMPLE)

Using the same blended resin as in Example 1, an extrusion was done using a round cross section die with a 0.057" land diameter and utilized the same tip used in Example 3 to allow a round bead (non-hollow) to be extruded. The barrel size was 0.650 inches and the mandrel was 0.315 inch, giving a calculated reduction ratio of 99 to 1 The barrel and die temperature was set to 45 degrees C. for this example. The wet extrudate was taken up using the method of Example 1. The spool of wet extrudate was placed on a tension payoff and processed in manner similar to example 1. Speed ratios used for this test are noted in Table 4.The fiber obtained using this process was tested for width, thickness, denier, and strength. The results are reported in Table 4. (Before the strength was measured, the samples were coated with 2% natural beeswax as described in connection with Example 1.)

EXAMPLE 5 (NON-HOLLOW FIBER INCLUDING AN ADDITIVE)

CD 123 PTFE resin was blended with 10% by weight of $SiO_2$. This resin was then blended with 320 ml/lb of isopropyl alcohol and allowed to sit overnight before pelletizing. A pre-form was compressed to a pressure of 300 psi for the 0.850-inch barrel and preheated to 45 degrees C. The pre-form was extruded using a 0.850-inch barrel, a 0.315-inch mandrel, a 0.098-inch land diameter die and a 0.050-inch land diameter tip. The calculated reduction ratio for this combination was 87 to 1. The barrel and die temperature was set to 45 degrees C. for this example. The wet extrudate was taken up and processed using the method of Example 1 with the following modifications: the first capstan rate was set to 2 ft/min, a single forced-air oven was used with an oven airflow of 10 cubic feet per minute, and an oven exit temperature of 375 degrees C. Separate examples were prepared with speed ratios of 2 to 1, 5 to 1, 10 to 1, 14 to 1, 18 to 1 and 27 to 1 to process the material. The samples produced using the process of this example was tested for width, thickness, denier, and strength. The results are reported in Table 5. (Before the strength was measured, the samples were coated with 2% natural beeswax as described in connection with Example 1.)

A comparative sample of J&J Reach® Easy Slide® Mint floss was tested for certain properties for comparison with those measured for the inventive samples. The results of the comparative sample measurements are reported in Table 6. As can be seen the inventive fiber under all but one set of conditions had a density considerably below that of the comparative sample.

Certain samples from the above examples were separately tested for abrasion resistance using the test described above. The inventive samples were coated with 2% natural beeswax before abrasion testing. The beeswax was applied to the samples using a winding and waxing machine model CE-1487 available from Cezona International, Inc., Spring City, Pa. The beeswax was heated to 97 degrees Celcius before it was applied to the samples. A comparative sample of J&J Reach® Easy Slide® Mint floss was also tested for abrasion resistance. The results are reported in Table 7.

The results show that the samples of the inventive fiber had a higher abrasion resistance than the comparative sample as shown by the higher denier-normalized break strength of the inventive fiber. When retested after the abrasion resistance testing, the inventive fiber also showed much higher retained strength. This value is reported as strength decay in Table 7. (Note that because the original fiber sample was broken in the abrasion test to determine break strength, a sibling sample run through the abrasion test was used for this comparison. Any apparent strength gain is considered within the experimental error and is reported as 0.) "Strength decay" is thus defined herein as the percent strength loss by a fiber after undergoing the abrasion test described herein. As shown in Table 7, the inventive fibers have an advantageously lower strength decay compared to the comparative sample. The significantly improved strength decay of the inventive floss over the comparative floss simulates performance in the mouth of a user. As a user moves the floss repeatedly between teeth, thereby subjecting the floss to abrasion, it is important that the floss retain as much strength as possible to help prevent breakage. More strength will be retained by the inventive floss as indicated by its improved strength decay.

Figure 8:
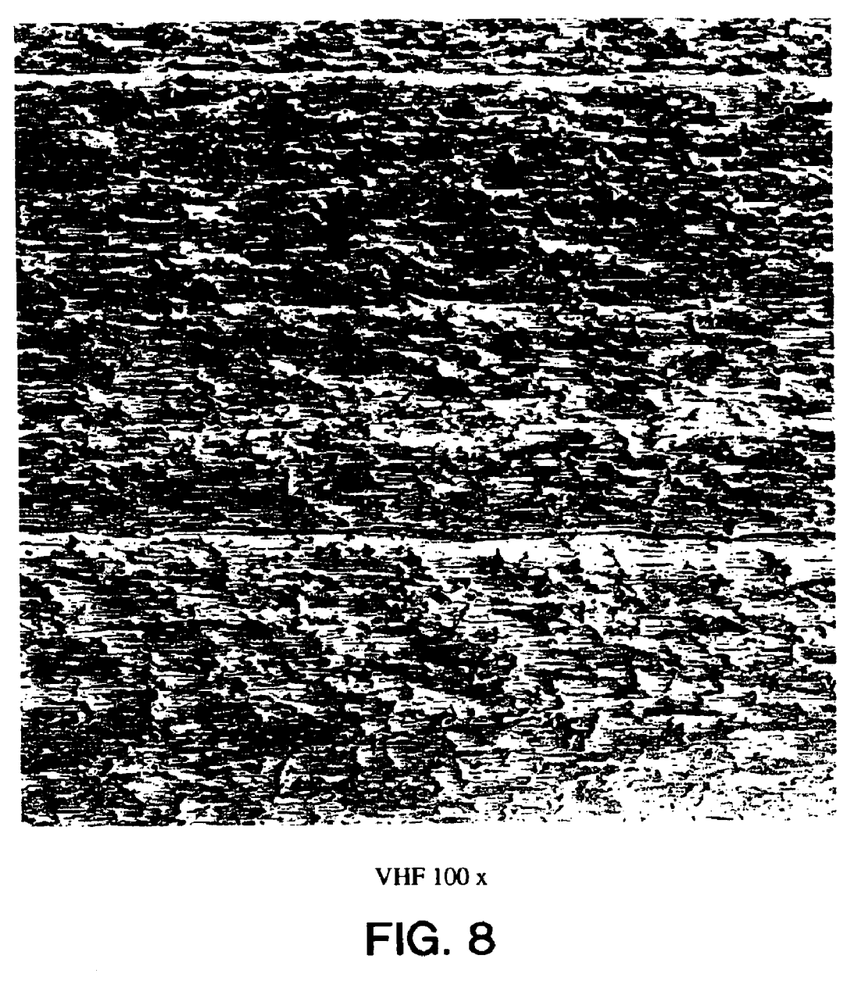
FIG. 8 is a scanning electron micrograph at 100× magnification of the surface of a sample of dental floss according to an exemplary embodiment of this invention.
Figure 9:
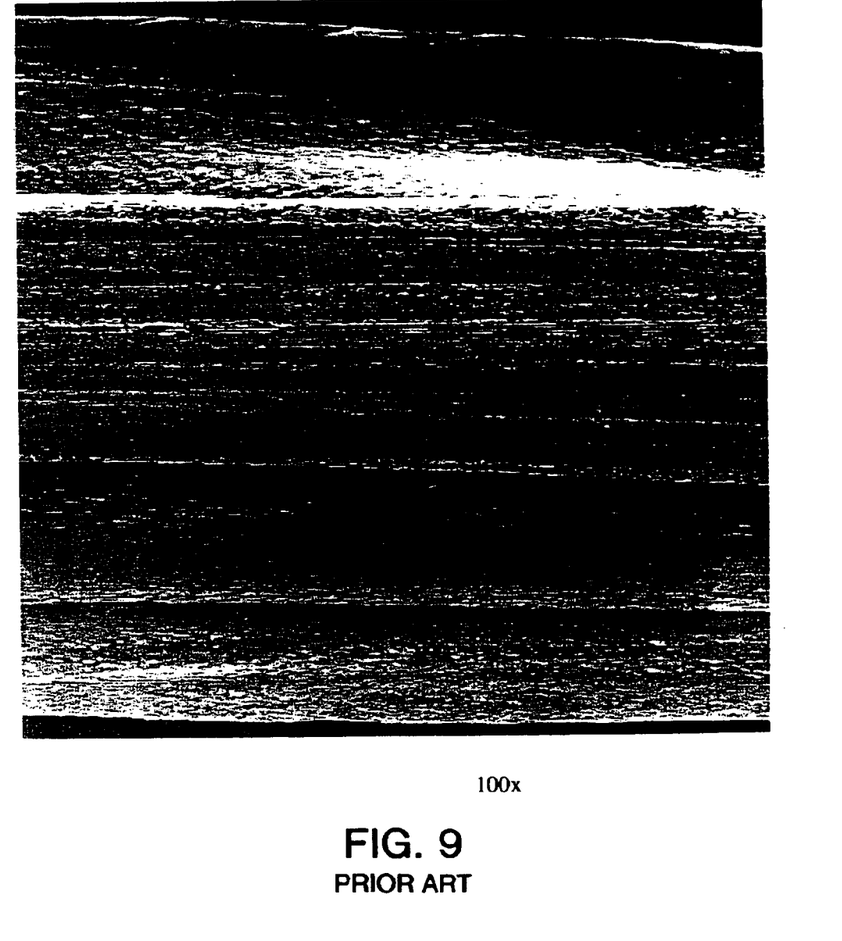
FIG. 9 is a scanning electron micrograph at 100× magnification of the surface of a sample of conventional, prior art dental floss.
Figure 10:
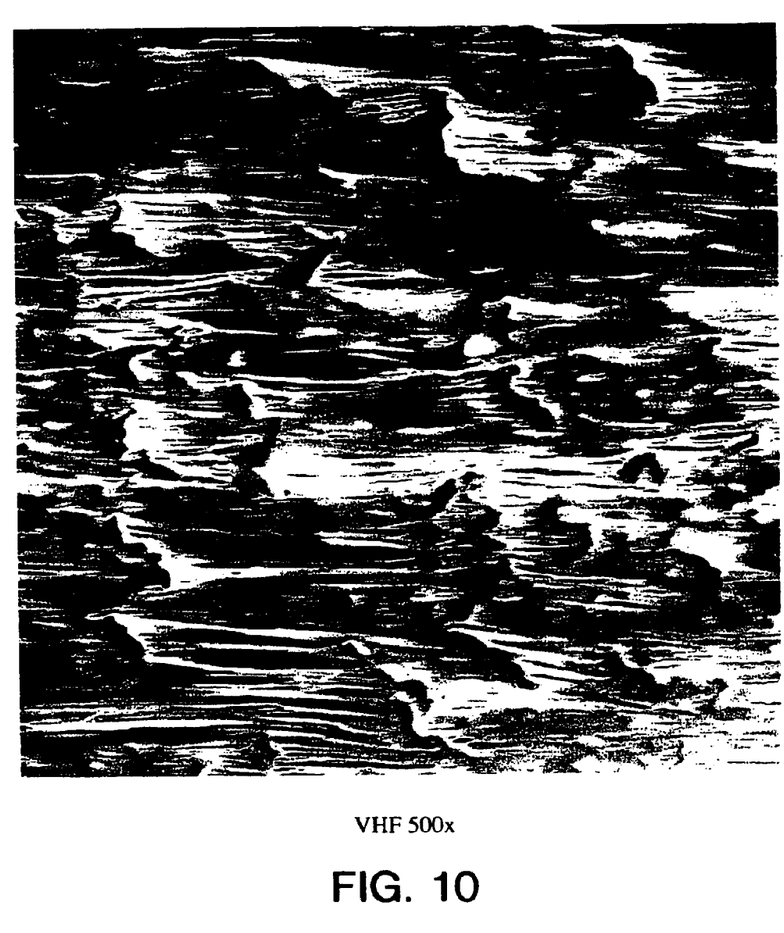
FIG. 10 is a scanning electron micrograph at 500× magnification of the surface of a sample of dental floss according to an exemplary embodiment of this invention.
Figure 11:
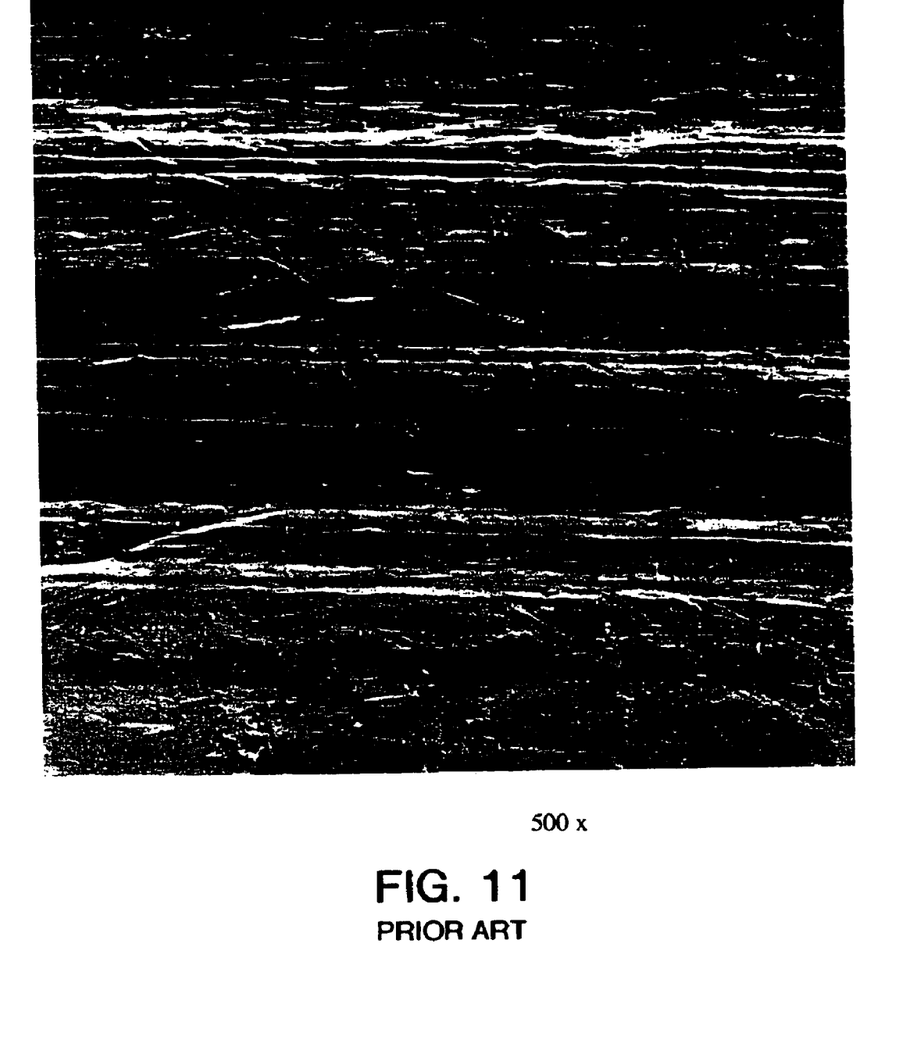
FIG. 11 is a scanning electron micrograph at 500× magnification of the surface of a sample of conventional, prior art dental floss.

FIG. 8 shows the surface of the inventive floss of Example 1 (the sample with a total speed ratio of 24 to 1) at 100× magnification. Significant surface roughness is visible. FIG. 8 is to be compared with FIG. 9, which shows the surface at the same magnification of a conventional PTFE floss (J&J Reach® Easy Slide® Mint floss after its surface coating has been stripped off by immersing the floss in xylene for 10 minutes and then air-drying the floss). The striking difference in surface morphology between the inventive floss of FIG. 8 and the comparative floss of FIG. 9 is surprising and unexpected. This unexpected result of such increased roughness of the surface morphology for the present invention is believed to produce the improved grippability, as well as other advantageous features, of the inventive floss. FIGS. 10 and 11 further illustrate the point by making the same comparison of surface morphology at 500× magnification. The surface of the inventive floss of Example 1 (the sample with a total speed ratio of 24 to 1) shown in FIG. 10 is seen to be significantly rougher than that of the comparative sample in FIG. 11 (J&J Reach® Easy Slide® Mint floss after its surface coating has been stripped off as described above).

The surface roughness of the inventive floss of Example 1 (the sample with a total speed ratio of 24 to 1) and the comparative sample (J&J Reach® Easy Slide® Mint) were measured. Both samples were prepared by immersing the floss in xylene for 10 minutes and then air-drying the floss. The results are reported below for the average roughness, the root mean square roughness, and the peak to valley ratio measured by the device under the conditions set forth above.

| Measurement | Inventive Fiber | J & J Reach ® Easy Slide ® Mint |
|---|---|---|
| Average Roughness (Ra) | 1.306 micron | .283 micron |
| Root Mean Square Roughness (Rq) | 1.570 micron | .348 micron |
| Peak to Valley (Rt.) | 6.316 micron | 1.706 micron |

As can be seen from the data, the inventive fiber shows considerably greater roughness than the comparative sample as measured by all of the reported features.

Again without being limited by theory, it is believed that the low density and other features of the inventive PTFE floss compared to conventional PTFE flosses contributes significantly to the improved properties of the floss. These features of the invention help provide a grippable floss that has a rough feel in the mouth for enhanced perceived effectiveness, along with a desirable soft, compressible feel to the hands, while providing considerable material savings in production. The inventors have discovered that existing PTFE flosses having a density of greater than 0.8 g/cc cannot be made to have lower density according to previously known production methods without significantly decreasing fiber strength. This invention provides a low density PTFE fiber having the advantages mentioned herein as well as having strength suitable for use as a dental floss.

As an additional advantage, the inventors have discovered that the dental floss of the present invention has an even greater perceived grippability when the floss is wet. This should further enhance a user's ability to grasp the floss during use.

As referenced above, a particularly advantageous application of the present floss is for use with a floss device. Because of the improved surface roughness and grippability of the inventive floss, devices may be molded having the inventive floss retained therein without the need for grip-enhancing coatings or additives. The inventors have produced samples of such floss devices, made of polypropylene substantially as described in European patent application publication number EP 922440 A2, with the inventive ePTFE floss, and the floss was adequately retained by the devices according to selected users in preference tests.

In addition, the inventive process and fiber may be used in a variety of other applications. Although described herein in connection with a monofilament floss, a multifilament floss may be produced with a plurality of fibers according to this invention. The inventive fiber may also be combined, such as by twisting or joined with a binder, with a conventional floss fiber to form a composite floss.

In addition, an improved sewing thread is provided using the present invention's high porosity characteristic. Sewing threads typically are coated or impregnated with a wax, oil or other lubricant to increase its processability during sewing operations. The increased porosity over traditional ePTFE sewing threads provides for the incorporation and application of higher amounts of the lubricants. Additionally, the increased rough surface morphology of the present invention provides for protected regions where lubrications and or other coatings may reside on the filament's surface. These regions may help to minimize the likelihood of the coatings being wiped off the filament's surface during sewing operations and other manufacturing and as well during the filament's use. An improvement to the duration of a lubricant or other coating or impregnation is believed to be increased as well due to the fiber's higher loading and its increased surface roughness.

The present invention also provides for an improved bearing and or bushing material due to the increased filament's porosity and the ability to impregnate the fibers with epoxies especially in the case of bushing. The filament is woven into a sock configuration and epoxy is applied around the woven sock. It is important that a bond between the woven sock and the epoxy is achieved. The present invention provides a surface which has increased surface roughness which permits the epoxy to adhere to. Additionally, the present invention's increased porosity provides for the epoxy or other flowable material to enter into the porous filament thus creating adhesion.

When filled with an electrical or a thermally conductive material, the invention provides for a filament with increased electrical and thermal resistance to density ratios. Moreover, since the present invention provides for filament with lower densities, the range in which one can vary the filler content and density either by subsequent compression or expansion or other means known in the art, the filament's conduction and its resistance can be more broadly varied.

While particular embodiments of the present invention have been illustrated and described herein, the present invention should not be limited to such illustrations and descriptions. It should be apparent that changes and modifications may be incorporated and embodied as part of the present invention within the scope of the following claims.

TABLE 1

| first ER | 2nd ER | total ER | Thickness (in) | Width (mm) | Weight (g/ft) | denier (g/9000 m) | density (g/cc) | Break Strength (lb) | Tenacity (g/denier) | MTS (psi) |
|---|---|---|---|---|---|---|---|---|---|---|
| 10 | 1.2 | 12 | 0.015 | 2.2 | 0.107 | 3159 | 0.42 | 10.2 | 1.47 | 40323 |
| 20 | 1.2 | 24 | 0.007 | 1.8 | 0.055 | 1624 | 0.56 | 7.8 | 2.18 | 59989 |
| 30 | 1.2 | 36 | 0.005 | 1.1 | 0.032 | 945 | 0.75 | 5.7 | 2.74 | 75346 |

ER = Expansion Ratio (results reported as a value to 1; i.e., a reported value of "10" means "10 to 1")
MTS = Matrix Tensile Strength

TABLE 2

| first ER | 2nd ER | total ER | Thickness (in) | Width (mm) | Weight (g/ft) | denier (g/9000 m) | density (g/cc) | Break Strength (lb) | Tenacity (g/denier) | MTS (psi) |
|---|---|---|---|---|---|---|---|---|---|---|
| 4 | 2.5 | 10 | 0.018 | 2.6 | 0.132 | 3898 | 0.36 | 13.5 | 1.57 | 43261 |
| 4 | 5 | 20 | 0.009 | 1.5 | 0.063 | 1860 | 0.60 | 8.8 | 2.15 | 59085 |
| 4 | 7.5 | 30 | 0.006 | 1 | 0.044 | 1299 | 0.95 | 7.4 | 2.59 | 71141 |
| 4 | 10 | 40 | 0.005 | 0.8 | 0.029 | 856 | 0.94 | 5.7 | 3.02 | 83141 |
| 4 | 15 | 60 | 0.005 | 0.5 | 0.022 | 650 | 1.14 | 4.3 | 3.01 | 82677 |

ER = Expansion Ratio (results reported as a value to 1; i.e., a reported value of "10" means "10 to 1")
MTS = Matrix Tensile Strength

TABLE 3

| first ER | 2nd ER | total ER | Thickness (in) | Width (mm) | Weight (g/ft) | denier (g/9000 m) | density (g/cc) | Break Strength (lb) | Tenacity (g/denier) | MTS (psi) |
|---|---|---|---|---|---|---|---|---|---|---|
| 10 | 1.2 | 12 | 0.017 | 1.5 | 0.079 | 2333 | 0.40 | 5.3 | 1.03 | 28379 |
| 20 | 1.2 | 24 | 0.01 | 1.3 | 0.039 | 1152 | 0.39 | 3.85 | 1.52 | 41758 |
| 30 | 1.2 | 36 | 0.006 | 1.3 | 0.028 | 827 | 0.46 | 2.7 | 1.48 | 40789 |
| 40 | 1.2 | 48 | 0.007 | 1.5 | 0.033 | 974 | 0.41 | 3.1 | 1.44 | 39736 |
| 40 | 2 | 80 | 0.008 | 0.7 | 0.037 | 1093 | 0.85 | 3 | 1.25 | 34297 |
| 40 | 2.5 | 100 | 0.003 | 0.3 | 0.01 | 295 | 1.44 | 1.3 | 2 | 54990 |

ER = Expansion Ratio (results reported as a value to 1; i.e., a reported value of "10" means "10 to 1")
MTS = Matrix Tensile Strength

TABLE 4

| first ER | 2nd ER | total ER | Thickness (in) | Width (mm) | Weight (g/ft) | denier (g/9000 m) | density (g/cc) | Break Strength (lb) | Tenacity (g/denier) | MTS (psi) |
|---|---|---|---|---|---|---|---|---|---|---|
| 20 | 1.2 | 24 | 0.01 | 1.1 | 0.041 | 1211 | 0.48 | 2.5 | 0.94 | 25793 |
| 30 | 1.2 | 36 | 0.007 | 1.1 | 0.023 | 679 | 0.39 | 2.2 | 1.47 | 40461 |
| 40 | 1.2 | 48 | 0.0045 | 1 | 0.019 | 561 | 0.55 | 1.6 | 1.29 | 35621 |
| 40 | 2 | 80 | 0.004 | 0.8 | 0.014 | 413 | 0.57 | 1.4 | 1.54 | 42300 |

ER = Expansion Ratio (results reported as a value to 1; i.e., a reported value of "10" means "10 to 1")
MTS = Matrix Tensile Strength

TABLE 5

| ER | thickness (inches) | Width (mm) | Weight/foot (g/ft) | Density (g/cc) |
|---|---|---|---|---|
| 0 | 0.035 | 3.9 | 0.828 | 0.78 |
| 2 | 0.033 | 3.5 | 0.378 | 0.42 |
| 5 | 0.023 | 3.3 | 0.185 | 0.32 |
| 10 | 0.008 | 3 | 0.042 | 0.23 |
| 14 | 0.013 | 2.9 | 0.07 | 0.24 |
| 18 | 0.013 | 3 | 0.027 | 0.1 |
| 27 | 0.009 | 2.6 | 0.045 | 0.25 |

ER = Expansion Ratio (results reported as a value to 1; i.e., a reported value of "10" means "10 to 1")

TABLE 6

| Comparative J & J Sample | | | | | | | | |
|---|---|---|---|---|---|---|---|---|
| Thickness (in) | Width (mm) | Weight (g/ft) | denier (g/9000 m) | density (g/cc) | Break Strength (lb) | Elongation at break (%) | Tenacity (g/denier) | MTS (psi) |
| 0.0015 | 2.7 | 0.044 | 1300 | 1.4 | 6.61 | 12.3 | 2.31 | 63546 |

MTS = Matrix Tensile Strength

TABLE 7

| Sample Source | Denier (g/9000 m) | Density (g/cc) | Break Strength (lbs) | Average Abrasion Break Strength (lbs) | Average Abrasion Break Strength per denier (× 1000) | Strength Decay (%) |
|---|---|---|---|---|---|---|
| Example 1 | 945 | 0.75 | 5.7 | 5.98 | 6.03 | 0 |
| Example 2 | 1299 | 0.95 | 7.4 | 7.16 | 5.47 | 3.2 |
| Example 3 | 1152 | 0.39 | 3.85 | 3.76 | 2.95 | 2.3 |
| Example 3 | 827 | 0.46 | 2.7 | 2.72 | 3.39 | 0 |
| J & J | 1300 | 1.4 | 6.61 | 4.18 | 2.77 | 37 |

What is claimed is:

1. A polytetrafluoroethylene (PTFE) fiber having a denier between 100 and 3500, a strength decay of less than 35%, and a density of less than about 0.8 g/cc.

2. A fiber as defined in claim 1, wherein said density is less than about 0.7 g/cc.

3. A fiber as defined in claim 1, wherein said density is less than about 0.6 g/cc.

4. A fiber as defined in claim 1, wherein said density is less than about 0.5 g/cc.

5. A fiber as defined in claim 1, wherein said density is less than about 0.4 g/cc.

6. A fiber as defined in claim 1, wherein said density is less than about 0.3 g/cc.

7. A fiber as defined in claim 1, wherein said density is less than about 0.2 g/cc.

8. A fiber as defined in claim 1, wherein said fiber comprises expanded PTFE.

9. A fiber as defined in claim 1, wherein said fiber has a strength suitable for use as a dental floss.

10. A fiber as defined in claim 1, wherein said fiber has a strength greater than about 1.5 lbs.

11. A fiber as defined in claim 1, wherein said fiber has a strength greater than about 2.0 lbs.

12. A fiber as defined in claim 1, wherein said fiber has a strength greater than about 2.5 lbs.

13. A fiber as defined in claim 1, wherein said fiber has a strength greater than about 3.0 lbs.

14. A fiber as defined in claim 1, wherein said fiber has a strength greater than about 5.0 lbs.

15. A fiber as defined in claim 1, wherein said fiber has a strength greater than about 7.5 lbs.

16. A fiber as defined in claim 1, wherein said fiber has a strength greater than about 10 lbs.

17. A fiber as defined in claim 1, wherein said fiber is hollow.

18. A fiber as defined in claim 1, wherein said fiber has a substantially elliptical cross-section.

19. A fiber as defined in claim 1, wherein said fiber has a substantially circular cross-section.

20. A fiber as defined in claim 1, wherein said fiber has a substantially rectangular cross-section.

21. A fiber as defined in claim 1, wherein said fiber has an average abrasion break strength greater than $2.8 \times 10^{-3}$ lbs per denier.

22. A fiber as defined in claim 1, wherein said fiber has an average abrasion break strength greater than $3.0 \times 10^{-3}$ lbs per denier.

23. A fiber as defined in claim 1, wherein said fiber has an average abrasion break strength greater than $4.0 \times 10^{-3}$ lbs per denier.

24. A fiber as defined in claim 1, wherein said fiber has an average abrasion break strength greater than $5.0 \times 10^{-3}$ lbs per denier.

25. A fiber as defined in claim 1, wherein said fiber has a strength decay of less than 10%.

26. A fiber as defined in claim 1, wherein said fiber has a strength decay of less than 5%.

27. A fiber as defined in claim 1, wherein said fiber contains at least one filler.

28. A fiber as defined in claim 27, wherein said fiber has a structure of an expanded PTFE matrix defining interconnected passages and pathways, and said filler is disposed in said passages and pathways.

29. A fiber as defined in claim 27, wherein said fiber has a structure of an expanded PTFE matrix defining interconnected passages and pathways, and said filler is disposed in said expanded PTFE matrix.

30. A fiber as defined in claim 27, wherein said fiber has a center bore and said filler is disposed in said center bore.

31. A fiber as defined in claim 27, wherein said filler comprises a grip enhancing material.

32. A fiber as defined in claim 27, wherein said filler is selected from bioactive ingredients, colorants, flavorants, medicants, gripping agents, anti-microbials, lubricants, and epoxies and flavor enhancers.

33. A fiber as defined in claim 27 further comprising at least one coating over said fiber.

34. A fiber comprising at least one fiber as defined in claim 27 land at least one other fiber, wherein said one fiber and said at least one other fiber are twisted together or joined together by a binder.

35. Fiber as defined in claim 27 wherein said fiber is formed as a sewing thread.

36. The sewing thread of claim 35, wherein said sewing thread is impregnated with a lubricant.

37. Fiber as defined in claim 27, wherein said fiber is formed as a bearing.

38. Fiber as defined in claim 27, wherein said fiber is formed as a bushing.

39. Fiber as defined in claim 27, wherein said fiber is a weaving fiber.

40. The weaving fiber as defined in claim 39, wherein said weaving fiber is woven into a sock configuration.

41. The weaving fiber as defined in claim 40, wherein epoxy is applied around the woven sock.

42. A fiber as defined in claim 1, having a thickness to width ratio of 1 or less.

43. A fiber comprising an expanded PTFE fiber having surface characteristics of an average roughness of about 1.3 microns, a root mean square roughness of greater than 0.35 microns, and a peak to valley distance of greater than 1.7 microns.

44. A fiber as defined in claim 43 wherein said root mean square roughness is about 1.570 microns.

45. A fibre as defined in claim 43 wherein said peak to valley distance is about 6.316 microns.

46. A fiber as defined in claim 1 wherein said fiber has a surface with an average roughness of about 1.3 microns, a root mean square roughness of about 1.6 microns, and a peak to valley distance of about 6.3 microns.

47. A fiber comprising PTFE having a surface area with a structure of nodes and fibrils, wherein, as shown in a scanning electron micrograph of the surface area, said nodes comprise between about 3% and about 20% of the surface area, and said fibrils have a mean length of less than 100 microns.

48. The fiber of claim 47 wherein the magnification of said scanning electron micrograph is ×100.

49. The filament of claim 47 wherein the magnification of said scanning electron micrograph is ×500.

* * * * *